United States Patent
Yoon et al.

(10) Patent No.: US 6,395,012 B1
(45) Date of Patent: May 28, 2002

(54) APPARATUS AND METHOD FOR DELIVERING AND DEPLOYING AN EXPANDABLE BODY MEMBER IN A UTERINE CAVITY

(76) Inventors: InBae Yoon, 11886 Farside Rd., Ellicott City, MD (US) 21042; Ronald J. Brinkerhoff, 3030 Twin Ridge Dr., New Richmond, OH (US) 45157; Hal H. Katz, 7903 Woodglen Dr., West Chester, OH (US) 45069; William J. Kraimer, 8037 Buckland Dr., Cincinnati, OH (US) 45249; Leo J. Nolan, 10805 Clarion La., Las Vegas, NV (US) 89134

(*) Notice: Subject to any disclaimer, the term of this patent is extended or adjusted under 35 U.S.C. 154(b) by 0 days.

(21) Appl. No.: 09/563,920

(22) Filed: May 4, 2000

(51) Int. Cl.[7] .............................................. A61M 17/00
(52) U.S. Cl. ..................................................... 606/193
(58) Field of Search ................................. 606/193, 192, 606/191, 41, 114, 105, 132

(56) References Cited

U.S. PATENT DOCUMENTS

| | | | | |
|---|---|---|---|---|
| 3,924,628 A | * | 12/1975 | Droegemueller et al. ...... 606/21 |
| 4,010,751 A | | 3/1977 | Ring ............................ 604/14 |
| 4,601,698 A | | 7/1986 | Moulding, Jr. ............... 128/831 |
| 4,772,274 A | | 9/1988 | Lukacs ........................ 604/275 |
| 5,084,044 A | * | 1/1992 | Quint ........................... 606/191 |
| 5,336,188 A | | 8/1994 | Kriesel ........................ 604/132 |
| 5,443,470 A | * | 8/1995 | Stern et al. .................. 606/32 |
| 5,451,208 A | * | 9/1995 | Goldrath ..................... 600/135 |
| 5,460,628 A | * | 10/1995 | Neuwirth et al. ............. 606/27 |
| 5,505,730 A | * | 4/1996 | Edwards ...................... 604/21 |
| 5,571,153 A | * | 11/1996 | Wallsten ...................... 607/98 |
| 5,613,950 A | | 3/1997 | Yoon .......................... 604/105 |
| 5,653,692 A | * | 8/1997 | Masterson et al. ........... 604/113 |
| 5,891,094 A | * | 4/1999 | Masterson et al. ........... 604/113 |
| 5,906,615 A | * | 5/1999 | Thompson .................... 606/41 |
| 5,935,056 A | * | 8/1999 | Kerin et al. .................. 600/114 |
| 5,954,714 A | * | 9/1999 | Saadat et al. ................. 606/28 |
| 6,002,968 A | | 12/1999 | Edwards ...................... 607/101 |
| 6,024,743 A | | 2/2000 | Edwards ...................... 606/42 |
| 6,053,913 A | * | 4/2000 | Tu et al. ....................... 600/585 |
| 6,086,584 A | * | 7/2000 | Miller ......................... 604/114 |
| 6,113,594 A | * | 9/2000 | Savage ........................ 128/898 |

OTHER PUBLICATIONS

"Hysteroscopy," Proceedings of the First European Symposium on Hysteroscopy, Sep. 2–3, 1982, Antwerp, Belgium, 1983 MTP Press Limited, pp. 11–32.

* cited by examiner

Primary Examiner—Teresa Walberg
Assistant Examiner—Daniel Robinson
(74) Attorney, Agent, or Firm—Blank Rome Comisky & McCauley LLP

(57) ABSTRACT

An apparatus and method delivers an expandable body member into a uterine cavity of a uterus through a cervical opening and deploys the expandable body member in the uterine cavity. The expandable body member in a compressed state is inserted into the uterine cavity. A fluid is provided to the uterine cavity at a pressure sufficient to inflate the uterine cavity. The expandable body member expands from the compressed state to the expanded state. After expansion of the expandable body member and inflation of the uterine cavity, the fluid pressure is relieved thereby collapsing the uterine cavity about the expandable body member in the expanded state such that an endometrial layer of the uterus and a surface of the expandable body member substantially contact each other in a facially opposing relationship maximizing contact therebetween. The apparatus which performs the method includes an elongated tubular member having the expandable body member connected to a distal portion of the elongated tubular member and a fluid-providing device connected to a proximal portion of the elongated tubular member.

26 Claims, 9 Drawing Sheets

APPARATUS AND METHOD FOR DELIVERING AND DEPLOYING AN EXPANDABLE BODY MEMBER IN A UTERINE CAVITY

FIELD OF THE INVENTION

The present invention relates to an apparatus and method for delivering and deploying an expandable body member in a uterine cavity. More particularly, the present invention is directed to an apparatus and method for delivering and deploying an expandable body member in the uterine cavity so that contact of the endometrial layer in the uterine cavity and the surface of the expandable body member in an expanded state is maximized.

BACKGROUND OF THE INVENTION

Ablation is a medical procedure which may be performed to treat one of many conditions such as abnormal bleeding of the endometrial layer of the uterus. To perform an ablation procedure, many types of ablation devices have been developed.

U.S. Pat. No. 5,769,880 to Truckai et al. teaches an apparatus and method for performing ablation of organs. The ablation apparatus includes an electrode carrying member that is mounted to a distal end of an elongated shaft. An array of electrodes is mounted to the surface of the electrode carrying member. After placement of the ablation apparatus in contact with the tissue to be ablated, a radio frequency generator is used to deliver radio frequency energy to the electrodes to induce current flow from the electrodes to the tissue to be ablated. The electrode carrying member is fabricated from a material which is, preferably, nonconductive, permeable to moisture, moisture absorbable and compressible. The electrode carrying member can be compressed to a smaller volume and subsequently released to its natural size upon elimination of the compression. Preferred materials for the electrode carrying member include open-cell sponge, foam, cotton, fabric, cotton-like material or any other material having the above-described characteristics.

U.S. Pat. No. 5,484,426 to Yoon teaches a multifunctional device used in endoscopic surgical procedures. The multifunctional device includes sponge material that is formed with a specific configuration to conform to a cavity wall to be cauterized. The multifunctional device also includes a tubular electrically conductive trunk with electrically conductive solid or tubular branches extending angularly therefrom which terminate at the peripheral surface of the sponge material when the sponge material is in a wet state. An electro-surgical probe is passed through the tubular trunk so that a unipolar electro-surgical device is produced with multiple electrodes defined at a peripheral surface of the sponge material. The multifunctional device is utilized to ablate or coagulate surface areas such as cystic cavities or the endometrium of a uterus.

In a non-pregnancy state, the uterus has a uterine cavity analogous to a freshly-ironed shirt pocket. In other words, opposing surfaces of the endometrial layer defining the uterine cavity contact each other in a facially opposing relationship thereby eliminating any useful space for performing ablation procedures. Thus, most ablation devices that are designed for insertion into the uterine cavity must create useful space therein. Particularly, it is beneficial that the portion of the ablation device inserted into the uterine cavity makes substantial contact with the endometrial layer. Particularly, with ablation devices using expandable body members such as the ones described above, expansion of the body member to its expanded state might not adequately expand the uterine cavity. Thus, contact between the endometrial layer and the surface of the expandable body member might be insufficient.

OBJECTS AND SUMMARY OF THE INVENTION

It is an object of the present invention to provide an apparatus and method for delivering an expandable body member into a uterine cavity of a uterus and deploying the expandable body member in the uterine cavity.

It is another object of the invention to provide an apparatus and method for delivering an expandable body member into the uterine cavity of the uterus and deploying the expandable body member in the uterine cavity such that contact between the endometrial layer and an expanded body member surface of the expandable body member in the expanded state is maximized.

Accordingly, an apparatus and method for delivering an expandable body member into a uterine cavity and deploying the expandable body member from its compressed state to its expanded state are hereinafter described. The apparatus of the invention delivers the expandable body member in a compressed state through the cervical opening and into the uterine cavity of a living body and deploys the expandable body member from the compressed state to the expanded state while the expandable body member is disposed in the uterine cavity. The apparatus includes an elongated tubular member and a fluid-providing device. The elongated tubular member has a distal portion, a proximal portion and an intermediate portion disposed between the distal portion and the proximal portion. The expandable body member is connected to the distal portion. The fluid-providing device is connected to the proximal portion of the elongated tubular member. The fluid-providing device is operative to provide a fluid to the uterine cavity through the elongated tubular member at a sufficient pressure to inflate the uterine cavity to a volume larger than the expandable body member in the expanded state. The provided fluid also causes the expandable body member to expand from the compressed state to the expanded state.

The method of the invention delivers the expandable body member into the uterine cavity of the uterus through a cervical opening and deploys the expandable body member in the uterine cavity which is defined by the endometrial layer. The expandable body member expands from a compressed state to an expanded state to form an expanded body member surface. One step of the method of the present invention is inserting the expandable body member in the compressed state through the cervical opening and into the uterine cavity. Another step provides a fluid to the uterine cavity at a pressure sufficient to inflate the uterine cavity. Another step causes the expandable body member to expand from the compressed state to the expanded state. Another step relieves the fluid pressure thereby allowing the uterine cavity to collapse about the expandable body member in the expanded state so that the endometrial layer and the expanded body surface substantially contact each other in a facially opposing relationship.

Other objects and advantages of the present invention will become apparent from the following description of the embodiments taken in conjunction with the accompanying drawings.

DETAILED DESCRIPTION OF THE EMBODIMENTS

Figures 1, 4:
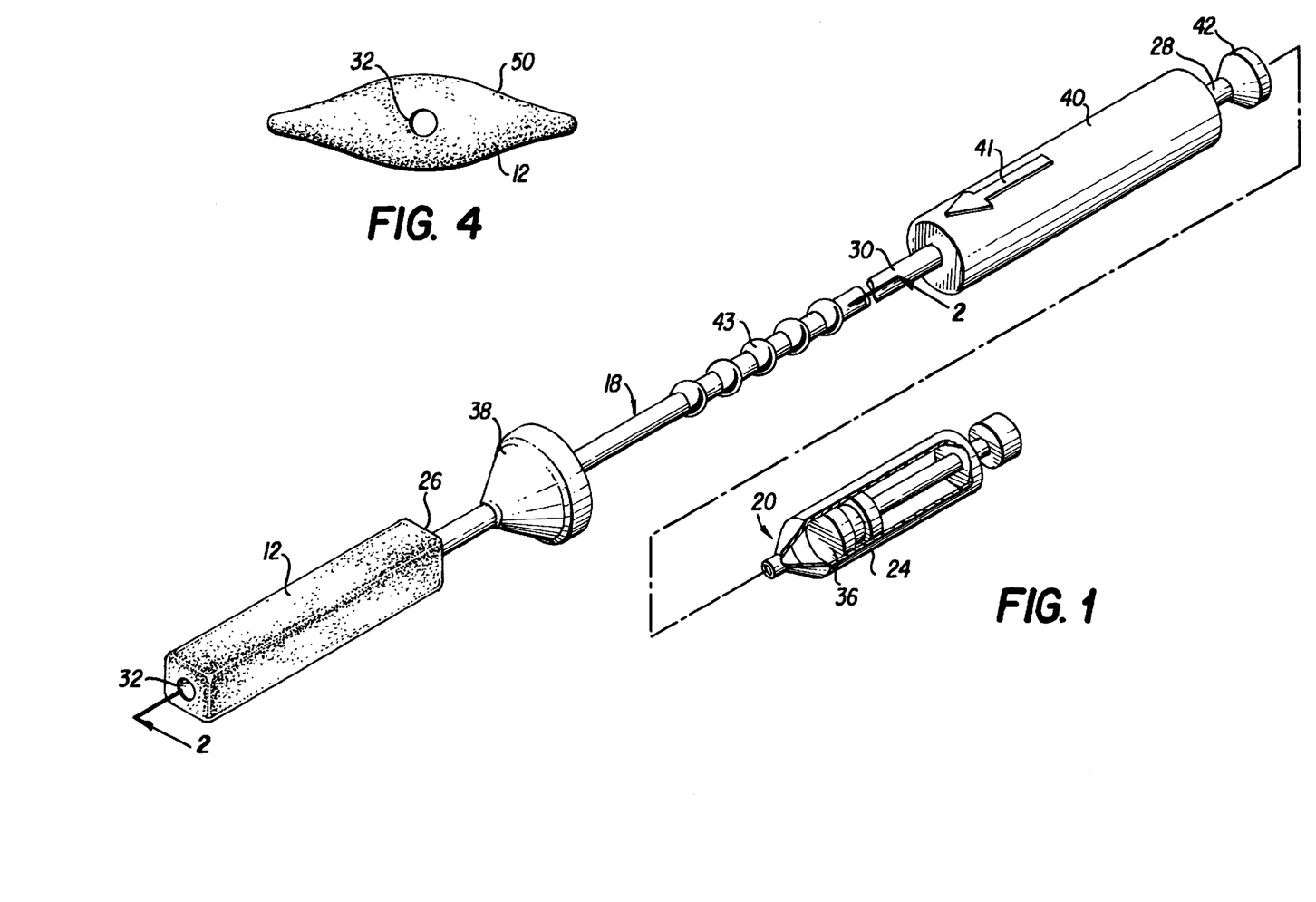
FIG. 1 is a perspective view of an apparatus of the present invention for delivering and deploying an expandable body member in a uterine cavity.
FIG. 4 is a top planar view of the expandable body member shown in FIG. 3.

An apparatus 10 of the present invention is generally introduced in FIGS. 1–4. As illustrated in FIGS. 5A–11B, the apparatus 10 of the present invention delivers an expandable body member 12 in a compressed state (FIGS. 1 and 2) through a cervical opening 14 and into a uterine cavity 16 of a uterus 17 of a living body. The apparatus 10 of the present invention also deploys the expandable body member 12 from the compressed state to an expanded state (FIGS. 3 and 4) while the expandable body member 12 is disposed in the uterine cavity 16 (FIGS. 7A–11B). As best shown in FIG. 1, the apparatus 10 of the present invention includes an elongated tubular member 18 and a fluid-providing device 20. Although not be way of limitation, the fluid-providing device 20 is illustrated as syringe assembly that includes a syringe 24.

Figure 2:
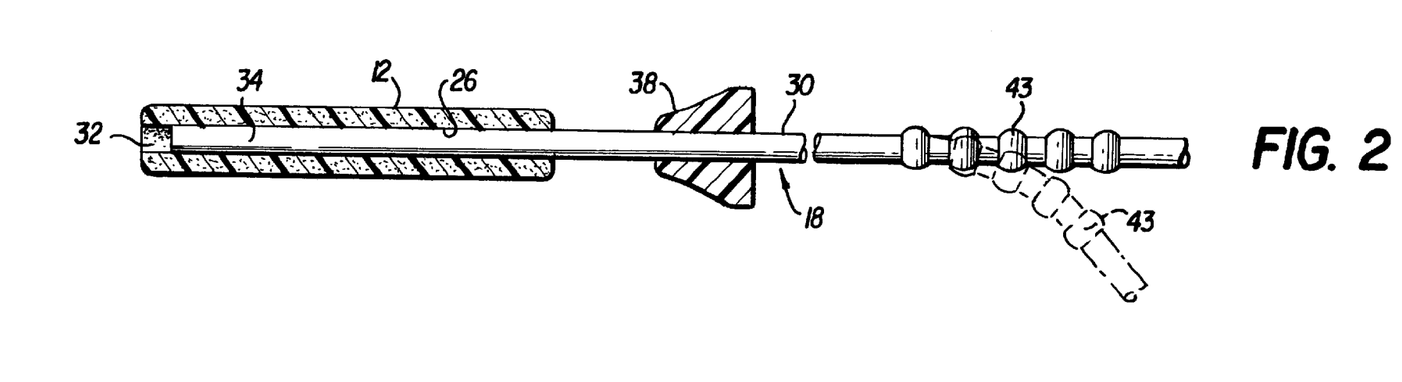
FIG. 2 is a partial cross-sectional view taken along line 2—2 in FIG. 1 with the expandable body member in a compressed state.
Figure 3:
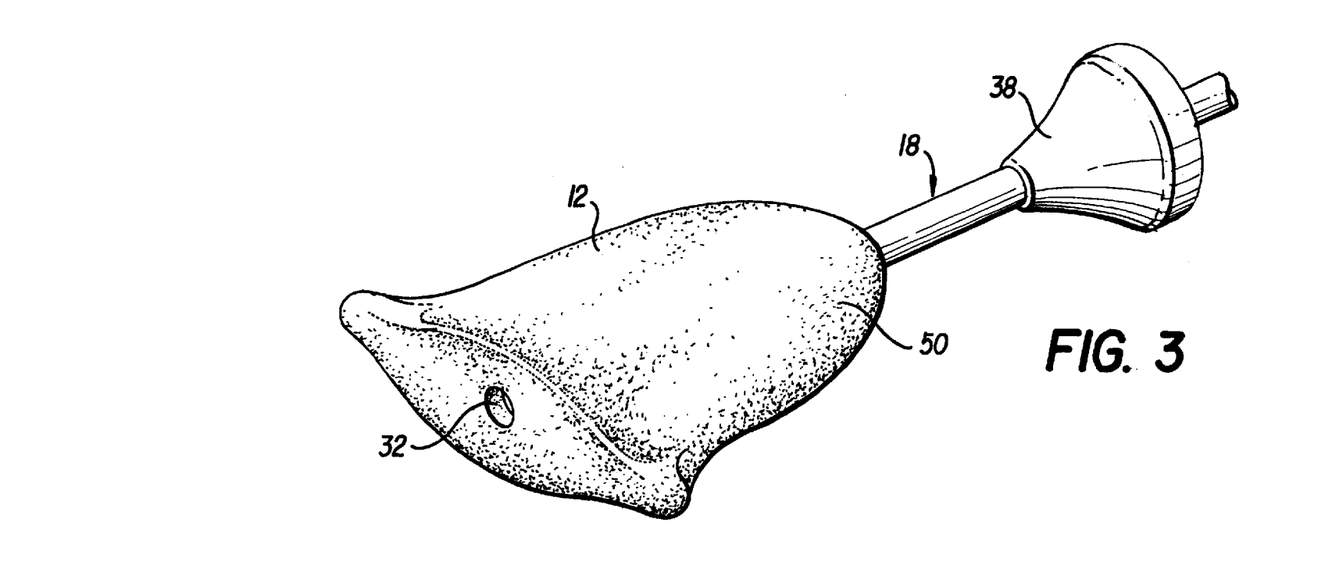
FIG. 3 is a perspective view of the expandable body member in an expanded state.

The elongated tubular member 18 has a distal portion 26 as best shown in FIG. 2, a proximal portion 28 and an intermediate portion 30 which is disposed between the distal portion 26 and the proximal portion 28 as shown in FIG. 1. The distal portion 26 and the expandable body member 12 are connected together while the expandable body member 12 is in the compressed state as illustrated in FIG. 2. A hole 32 is formed in the expandable body member 12 and is in fluid communication with a lumen 34 defined by the elongated tubular member 18.

With reference to FIG. 1, the fluid-providing device 20 is connectable to the proximal portion 28 of the elongated tubular member 18 and contains a fluid 36. One of ordinary skill in the art would appreciate that the fluid 36 would typically be a saline solution in liquid form. However, other fluid-providing devices as is known in the art might contain a gaseous fluid or a moisture-laden gaseous fluid. The fluid-providing device 20 provides the fluid 36 into the uterine cavity 16 through the lumen 34 of the elongated tubular member 18 and through the hole 32 of the expandable body member 12 at a sufficient pressure to inflate the uterine cavity 16 to a volume larger than the expandable body member in the expanded state shown in FIGS. 10A–10B and discussed in more detail below. The provided fluid 36 not only inflates the uterine cavity 16 but also causes the expandable body member 12 to expand from the compressed state (FIGS. 1 and 2) to the expanded state (FIGS. 3 and 10A–11B).

Further, the fluid-providing device 20 for this embodiment of the present invention includes a fitting 42 as shown in FIG. 1. The fitting 42 is connected to the proximal portion 28 of the elongated tubular member 18 and secures the syringe 24 to the proximal portion 28 of the elongated tubular member 18. In lieu thereof, one of ordinary skill in the art could appreciate other types of fitting and syringe assemblies can be used. A commonly used fitting and syringe assembly known in the art is a Luer Lok® syringe assembly. Leur Lok® is a U.S. registered trademark of Becton, Dickenson and Company of Franklin Lakes, N.J.

As is commonly known in the art, the fluid-providing device 20 in the form of the syringe assembly described above is not only capable of providing the fluid 36 to the uterine cavity 16 at a sufficient pressure to inflate it, but also, the syringe assembly can be used to withdraw the fluid 36 from the uterine cavity 16 thereby relieving the fluid pressure inside the uterine cavity 16 after the uterine cavity 16 is inflated.

The apparatus 10 of the present invention also includes a plug element 38. As best shown in FIGS. 8A-10B, the plug element 38 is sized and adapted to plug the cervical opening 14 into the uterine cavity 16 in order to prevent the fluid 36 from escaping the uterine cavity 16 upon inflation thereof. The plug element 38 is connected to the intermediate portion 30 of the elongated tubular member as shown in FIG. 1. The apparatus 10 of the present invention also includes a handle 40 which is also connected to the intermediate portion 30 of the elongated tubular member 18. Although not by way of limitation, the handle 40 is cylindrically shaped and is disposed between the plug element 38 and the proximal portion 28 of the elongated tubular member 18. Further, the handle 40 includes an indicator 41 in a form of an arrow. The indicator 41 indicates to a user an approximate orientation of the expandable body member 12 as it is disposed within the uterine cavity 16. The indicator 41 in the form of an arrow is illustrated by way of example only and that a skilled artisan would appreciate that other indicators such other indicia or a physical element can be used on the handle 40 or some other section of the apparatus 10 positioned exteriorly of the living body to indicate to the user the approximate orientation of the expandable body member 12 as it is disposed within the uterine cavity 16.

As shown in FIGS. 1 and 2, the elongated tubular member 18 includes an articulating joint 43 disposed between the handle 40 and the plug element 38. A skilled artisan would appreciate that the articulating joint 43 is operative to permit the elongated tubular member 18 to bend to alleviate discomfort that might result to the patient upon insertion of the expandable body member 12 into the uterus 17. Although not by way of limitation, the articulating joint 43 is illustrated as an integral construction with the elongated tubular member 18. However, the articulating joint 43 can be a separate component interposed in the elongated tubular member 18.

Another embodiment of the present invention is a method that delivers the expandable body member 12 into the uterine cavity 16 of a uterus 17 through the cervical opening 14 and deploys the expandable body member 12 in the uterine cavity 16. The method of the present invention is illustrated sequentially in FIGS. 5A–B through 11A–B.

Figures 5A, 5B:
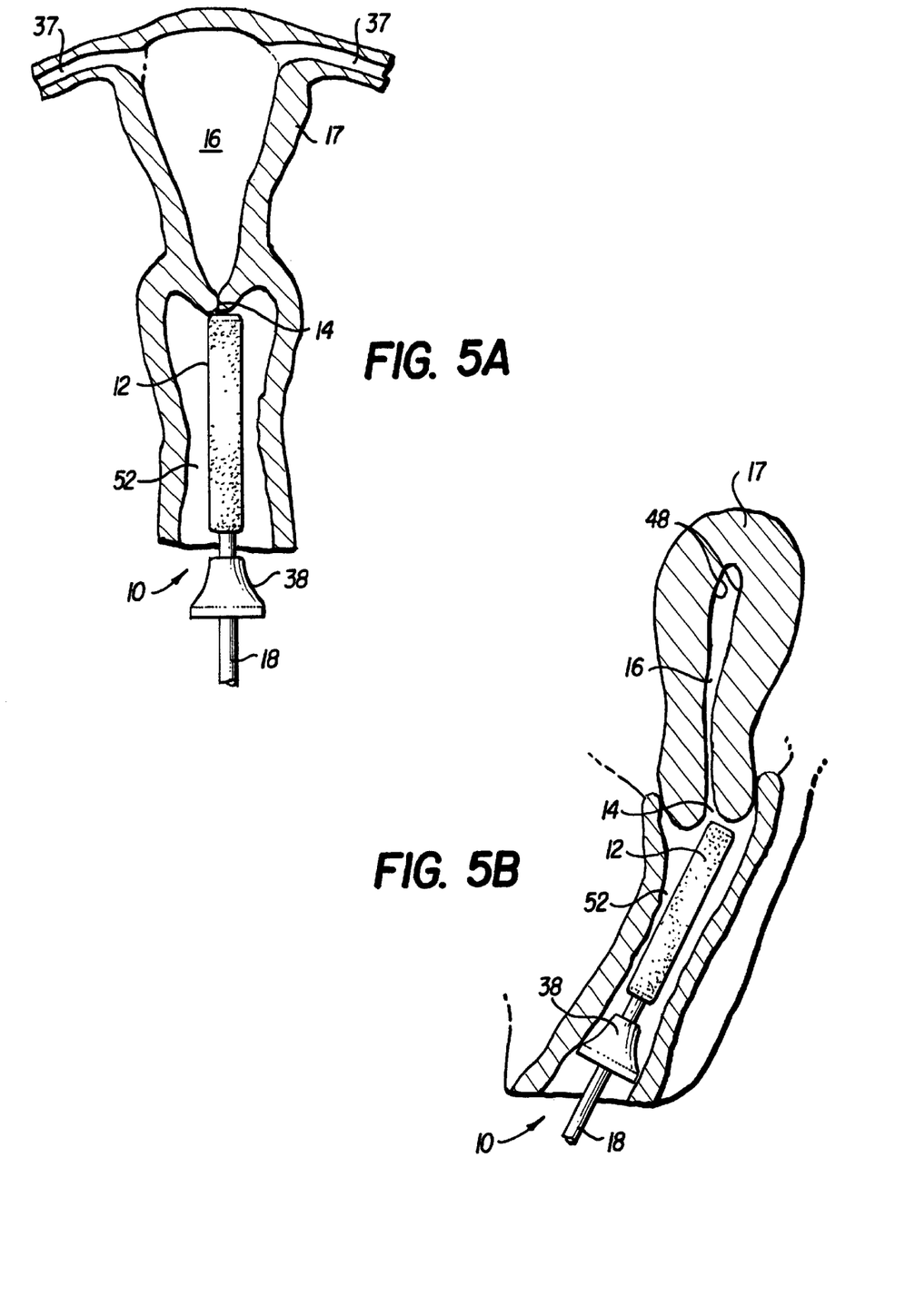
FIGS. 5A–5B are diagrammatic views illustrating the expandable body member in the compressed state positioned adjacent a cervical opening of a uterus.
Figures 6A, 6B:
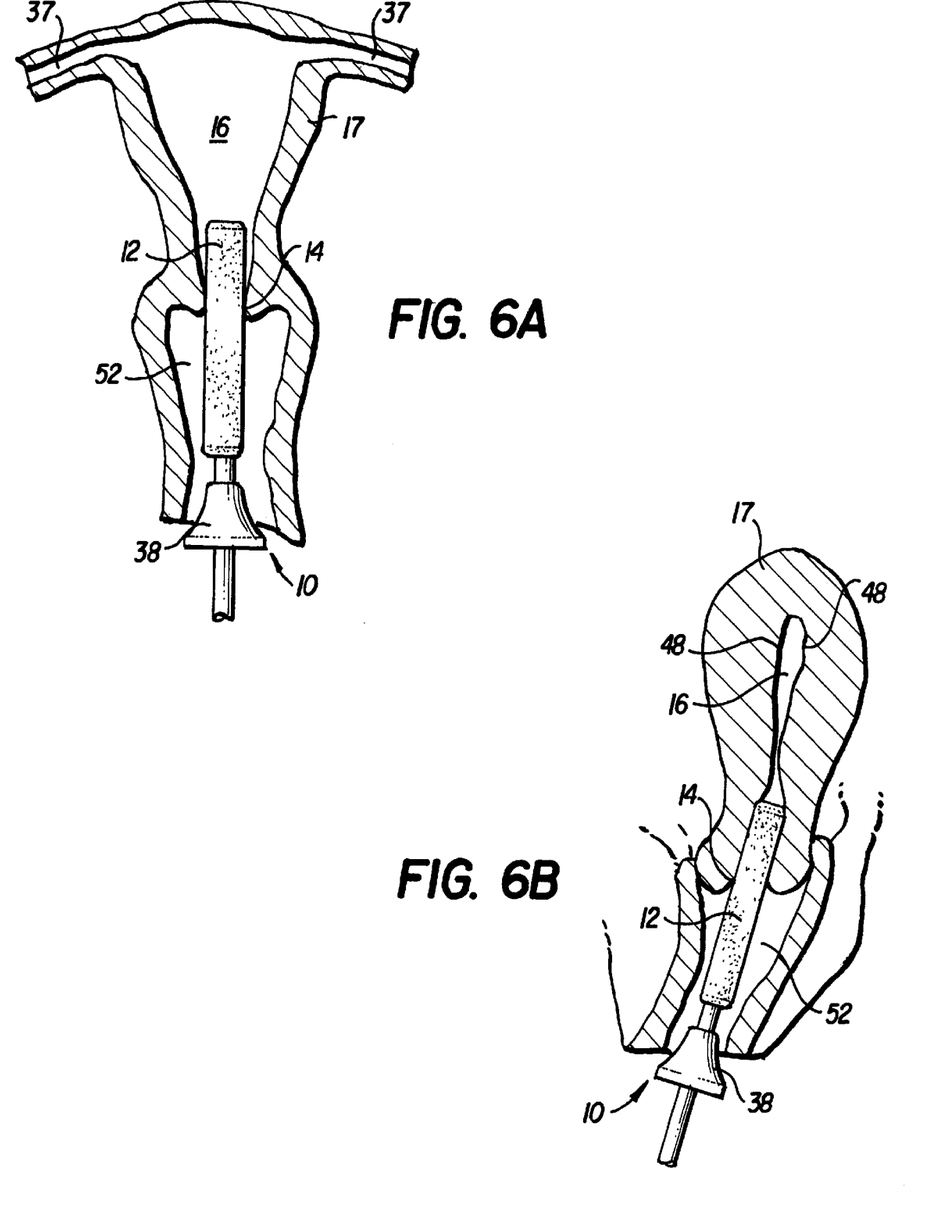
FIGS. 6A–6B are diagrammatic views of the expandable body member in the compressed state being inserted through the cervical opening and into a uterine cavity of the uterus.

As shown in the "B" series of FIGS. 5B–10B, the uterine cavity 16 is defined by an endometrial layer 48. Further, the expandable body member 12 expands from the compressed state to the expanded state to form an expanded body member surface 50 as shown in FIGS. 3 and 10A–11B. In FIGS. 5A–5B, the apparatus 10 is partially disposed within a vaginal canal 52 with an end of the expandable body member 12 positioned adjacent the cervical opening 14. The expandable body member 12 has a first configuration which is sized and adapted to be inserted through the cervical opening 14 preferably in a dry condition. Although not be way of limitation, the expandable body member 12 in the compressed state is sufficiently stiff to maintain its shape while it is inserted into the cervical opening 14. Preferably, a distal end portion of the expandable body member 12 is lubricated with a lubricant such as K-Y Jelly® to facilitate ease of insertion of the expandable body member 12 through the cervical opening 14 and into the uterine cavity 16. K-Y Jelly® is a federally registered trademark of Johnson & Johnson of New Brunswick, N.J. Also, the lubricant also maintains the expandable body member 12 in the dry condition during insertion, thus, preventing premature expansion of the expandable body member 12 from the compressed state. A skilled artisan would appreciate that other means, such as a removable sheath, are available to maintain the expandable body member 12 in the dry state during insertion. In FIGS. 6A–B, the expandable body member 12 in the compressed state is inserted into the uterine cavity 16 through the cervical opening 14. Note that as the expandable body member 12 in the compressed state is inserted into the uterine cavity 16, useful space shown by the solid, inverted U-shaped line is created within the uterus 17.

Figure 7A:
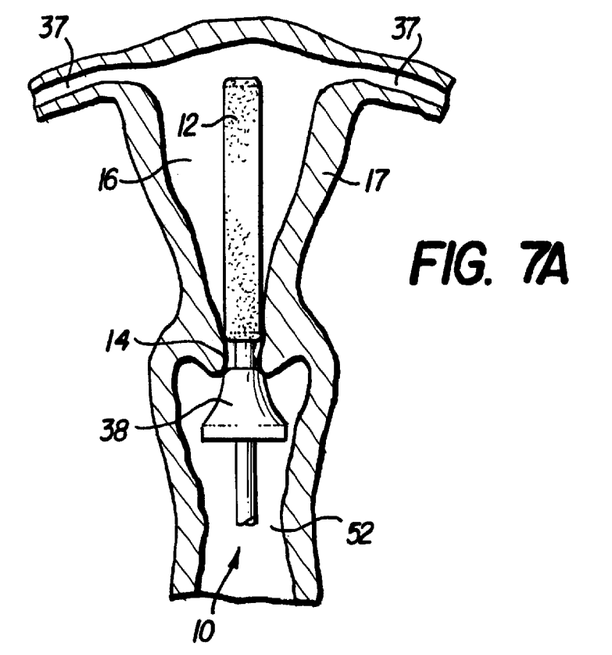
FIGS. 7A–7B are diagrammatical views of the expandable body member in the compressed state disposed within the uterine cavity with a plug element plugging the cervical opening.
Figure 7B:
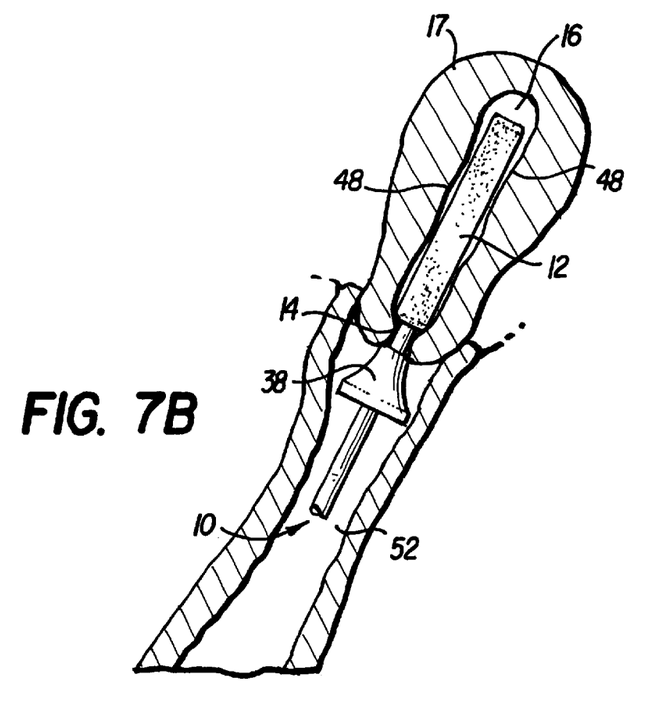
Figure 8A:
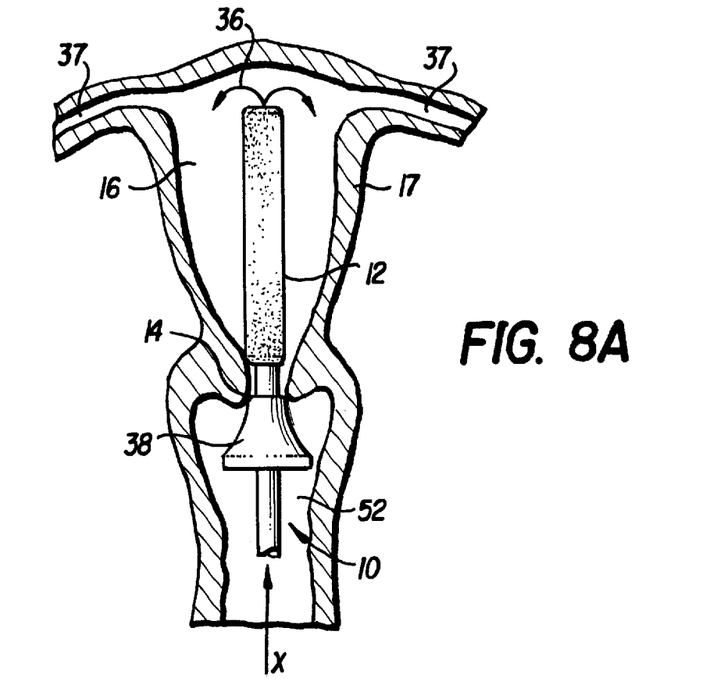
FIGS. 8A–8B are diagrammatic views of a fluid entering into and creating space within the uterine cavity.
Figure 8B:
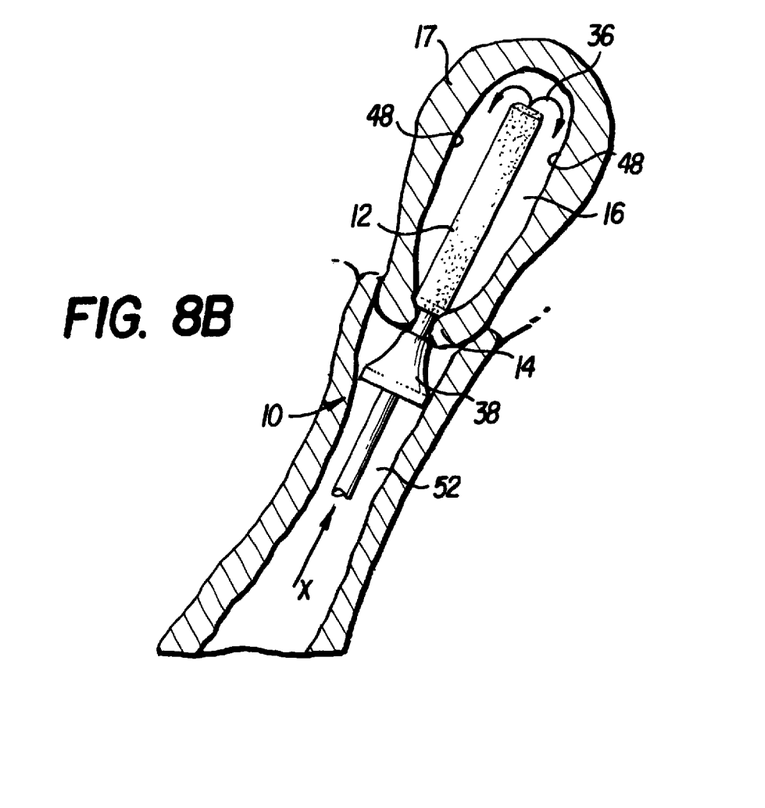

In FIGS. 7A–B, the expandable body member 12 in the compressed state is enveloped by the uterine cavity 16 while the plug element 38 plugs the cervical opening 14. In FIGS. 8A–B, the fluid 36 (depicted as arrows) is provided to the uterine cavity 16 by the apparatus 10 of the present invention described above. However, one of ordinary skill in the art would appreciate that the fluid 16 could be provided to the uterine cavity 16 by other devices commonly known in the art. The fluid 36 is provided at a pressure (represented by arrow "X") sufficient to inflate the uterine cavity 16 as shown in FIGS. 8A–10B. As illustrated by the solid lines propagating toward the dashed lines in FIG. 8A, initially, the provided fluid 36 creates more useful space within the uterine cavity 16. Preferably, the fluid pressure X is selected from a range of fluid pressure values between approximately 50 millimeters of mercury and 100 millimeters of mercury. A skilled artisan would appreciate that a conventional pressure gauge (not shown) can be used to monitor the fluid pressure. It is preferred that the fluid pressure value does not cause a patient pain or discomfort. However, the preferred pressure value would vary depending upon the muscular structure of the uterus, tolerance for pain by the patient, fluid leakage through fallopian tubes 37 and other variables. Further, as mentioned above, the provided fluid 16 can be either liquid, gaseous or even a moistened gaseous fluid. Also, it is appreciated that plugging the cervical opening 16 occurs before providing the fluid 36 to the uterine cavity 16 in order to prevent leakage of the fluid 16 through the cervical opening 14 and to prevent an undesirable loss of fluid pressure. Additionally, the elongated tabular member 18 can be fabricated from a malleable material such as metal or plastic, particularly, at the distal portion 26, so that the expandable body member 12 and the distal portion 26 can conform more closely to the natural curvature of the uterine cavity 16.

Figure 10A:
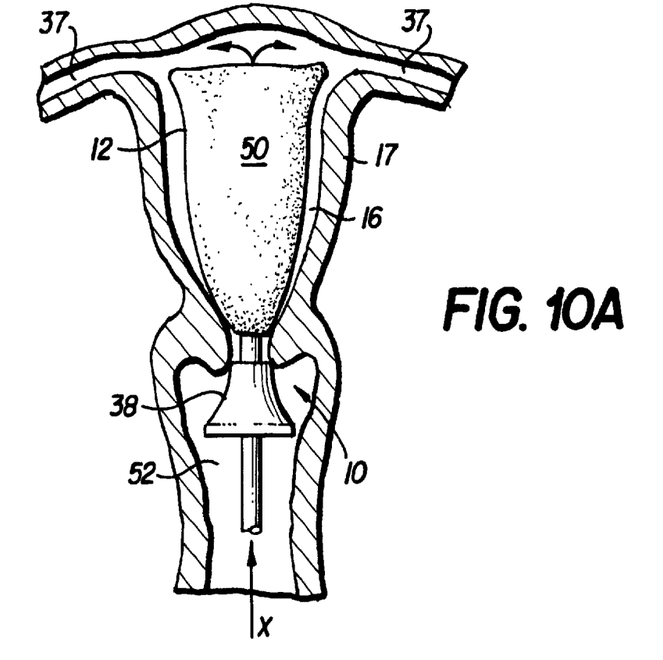
FIGS. 10A–10B are diagrammatic views of the expandable body member expanded to its fully expanded state while the uterine cavity is inflated under fluid pressure.
Figure 10B:
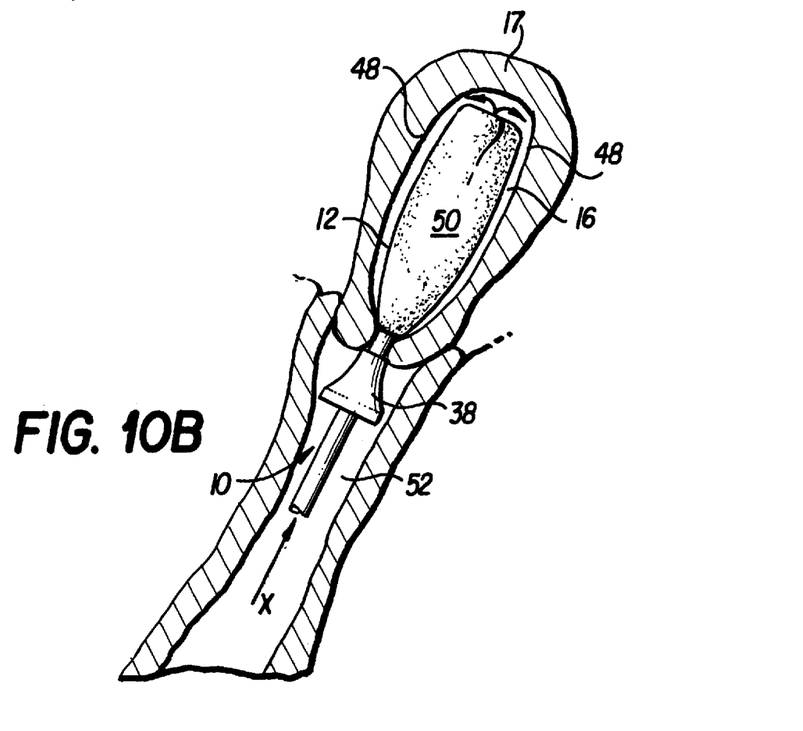

Preferably, the provided fluid 36 causes the expandable body member 12 to expand from the compressed state (FIGS. 7A–8B) to the expanded state (FIGS. 10A–B). With the provided fluid 36 as either a liquid or a moistened gas, it is preferred that the expandable body member 12 could be fabricated from a hydrophilic sponge material such as polyvinyl alcohol sponge. For the method of the present invention, the expandable body member 12 is hydrated by the provided fluid 36 causing the expandable body member to expand from the compressed state to the expanded state. It is appreciated that hydrating occurs when the expandable body member 12 is contacted by the provided fluid 36.

Figures 9A, 9B:
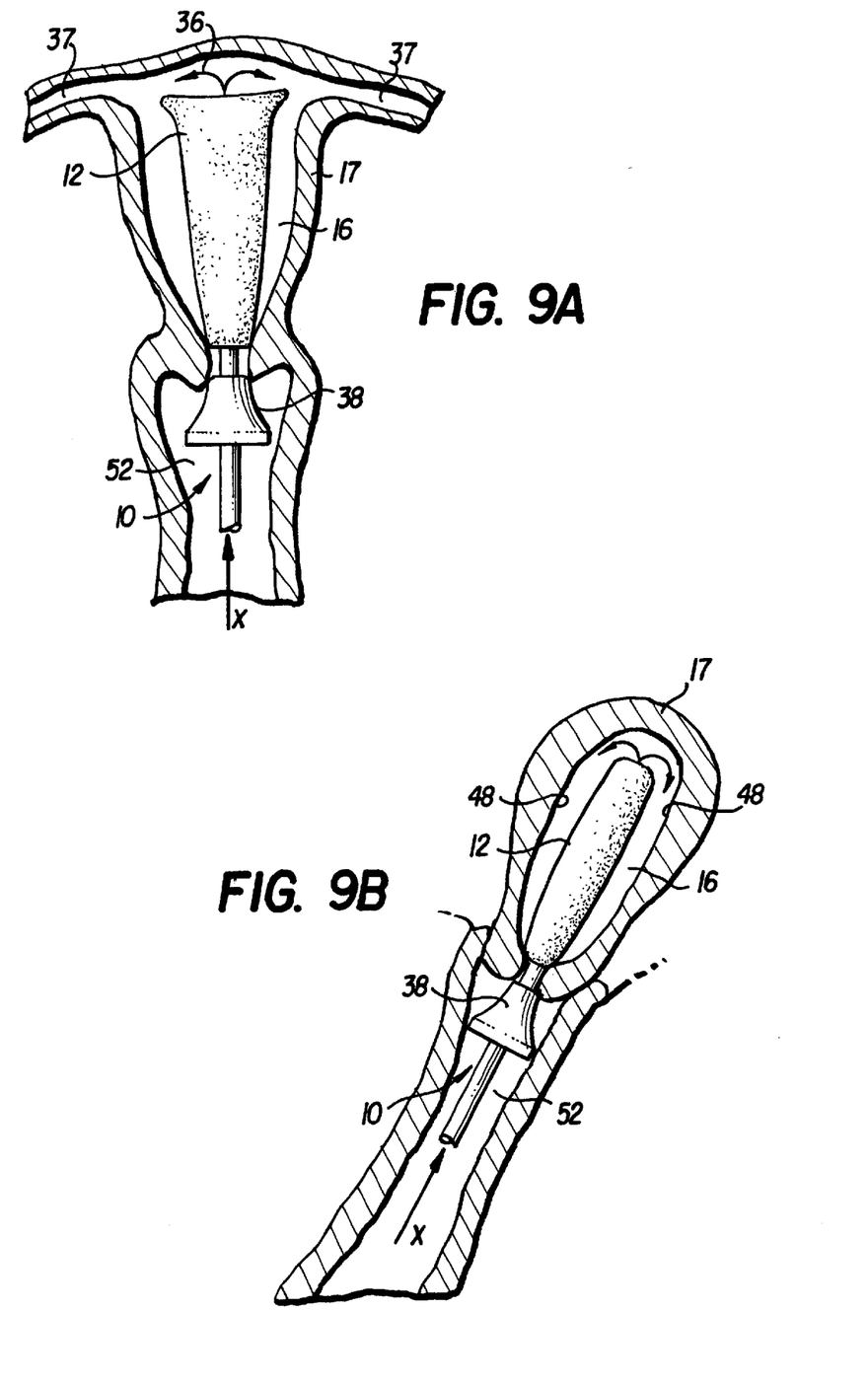
FIGS. 9A–9B are diagrammatic views illustrating the fluid causing the expandable body member to expand from its compressed state to its expanded state while disposed in the uterine cavity.

In FIGS. 9A–B, the provided fluid 36 under pressure X continues to create open space within the uterine cavity 16 while the expandable body member expands from the compressed state to the expanded state. In FIGS. 10A–B, the expandable body member 12 expands to its expanded state while the provided fluid 36 under pressure further inflates the uterine cavity 16. For explanation purposes, the inflated uterine cavity 16 has a cavity volume and the expandable body member 12 in the expanded state has a body member volume. At this stage, the cavity volume of the inflated uterine cavity 16 is larger than the body member volume of the expandable body member 12 in the expanded state. Furthermore, the expandable body member 12 in the expanded state has a second configuration that is different from the first configuration of the expandable body member 12 in the compressed state. Particularly, the expandable body member in the expanded state (i.e. the second configuration) is sized and adapted to conform to a shape of the uterine cavity 16 when the useful space is created. Also, the expandable body member 12 in the expanded state is preferably in a wet condition.

Figure 11A:
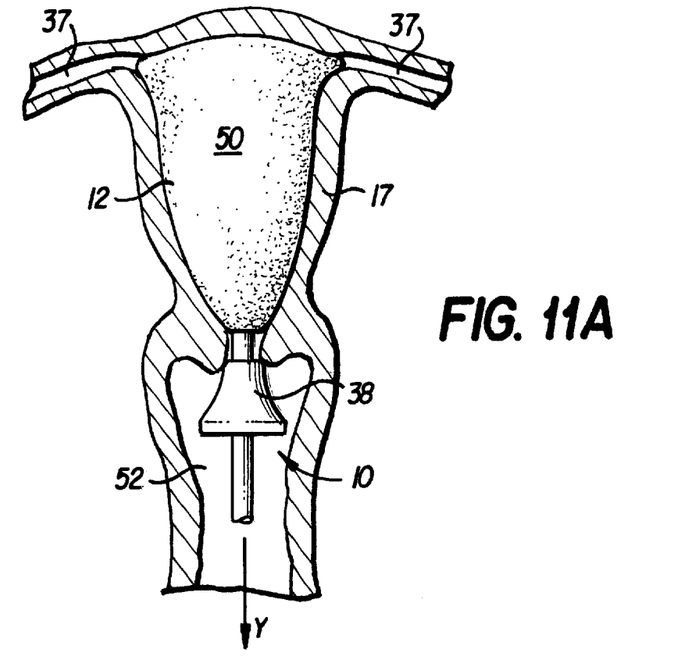
FIGS. 11A–11B are diagrammatical views of the uterine cavity collapsed upon the expandable body in the expanded state after relieving fluid pressure.
Figure 11B:
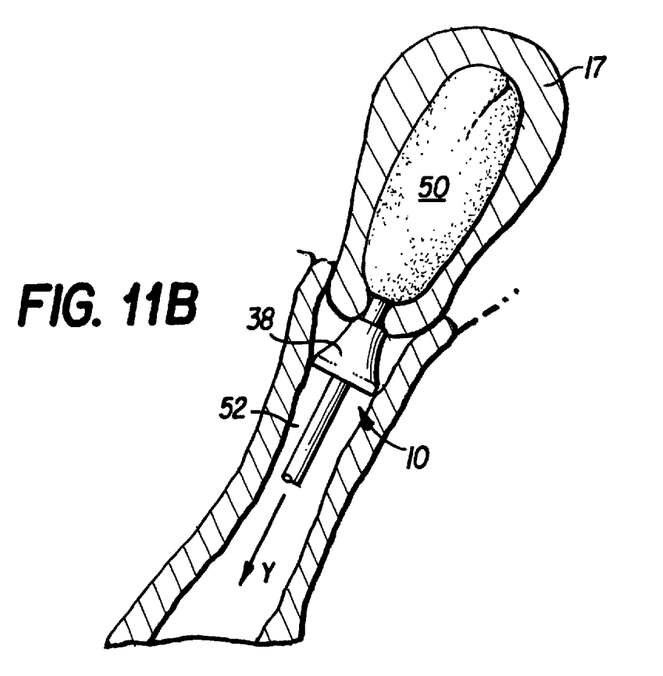

After the expandable body member 12 is expanded to the expanded state and the uterine cavity 16 is inflated, then, the fluid pressure is relieved as illustrated by arrow "Y" shown in FIGS. 11A–B. Once the fluid pressure is relieved, the uterine cavity 16 collapses about the expandable body member in the expanded state and wet condition. Thus, the endometrial layer 48 and the expanded body member surface 50 of the expandable body member 12 substantially contact each other in a facially opposing relationship as best illustrated in FIGS. 11A–B to maximize contact therebetween. Collapsing the uterine cavity 16 about the expandable body member 12 in the expanded state tends to compress the expandable body member 12 in the expanded state thereby compressing the expandable body member 12 toward the compressed state. However, the expandable body member 12 in the expanded state is resiliently biased towards the expanded state and the desired maximized contact is maintained.

The apparatus and method of the invention delivers the expandable body member into the uterine cavity and deploys it in a manner to provide maximum contact between the expandable body member and the endometrial layer. Such contact is desirable for performing ablation procedures or treatment. Furthermore, other mechanical devices such as spines are no longer required to assist in expanding the expandable body member in the uterine cavity.

Although the embodiments of the invention have been specifically described herein, it will be apparent to those skilled in the art to which the inventions pertain that other variations and modifications of the embodiments shown and described herein may be made without departing from the spirit and scope of the invention.

What is claimed is:

1. A method for delivering an expandable body member into a uterine cavity of a uterus through a cervical opening and deploying the expandable body member in the uterine cavity defined by an endometrial layer, the expandable body member expandable from a compressed state to an expanded state forming an expanded body member surface, the method comprising the steps of:

inserting the expandable body member in the compressed state through the cervical opening and into the uterine cavity;

providing a fluid to the uterine cavity at a pressure sufficient to inflate the uterine cavity;

causing the expandable body member to expand from the compressed state to the expanded state; and relieving the fluid pressure thereby collapsing the uterine cavity about the expandable body member in the expanded state so that the endometrial layer and the expanded body member surface substantially contact each other in a facially opposing relationship.

2. A method according to claim 1, wherein the inflated uterine cavity has a cavity volume and the expandable body member in one of the compressed state and expanded state has a body member volume, the cavity volume being larger than the body member volume.

3. A method according to claim 1, wherein the expandable body member in the compressed state has a first configuration and the expandable body member in the expanded state has a second configuration different from the first configuration.

4. A method according to claim 3, wherein the first configuration is sized and adapted to be inserted through the cervical opening.

5. A method according to claim 3, wherein the second configuration is sized and adapted to conform to a shape of the uterine cavity when the endometrial layer and the expanded body member surface substantially contact each other.

6. A method according to claim 1, wherein the expandable body member in the compressed state has a first configuration and is sized and adapted to be inserted through the cervical opening in a dry condition and the expandable body member in the expanded state has a second configuration different from the first configuration and is sized and adapted to conform to a shape of the uterine cavity in a wet condition when the endometrial layer and the expanded body member surface substantially contact each other.

7. A method according to claim 6, wherein the second configuration is sized and adapted to conform to a shape of the uterine cavity when the endometrial layer and the expanded body member surface substantially contact each other.

8. A method according to claim 1, wherein the expandable body member in the compressed state is dry and the expandable body member in the expanded state is wet.

9. A method according to claim 1, wherein the expandable body member is fabricated from a sponge material.

10. A method according to claim 1, wherein the expandable body member in the compressed state is stiff.

11. A method according to claim 1, wherein the expandable body member in the expanded state is resiliently biased toward the expanded state.

12. A method according to claim 1, wherein the step of causing the expandable body member to expand includes the step of hydrating the expandable body member when the expandable body member is in the compressed state.

13. A method according to claim 12, wherein the step of hydrating includes contacting the expandable body member with the provided fluid.

14. A method according to claim 1, wherein the provided fluid is one of a liquid fluid, a gaseous fluid and a moistened gaseous fluid.

15. A method according to claim 1, wherein the expandable body member is fabricated from a hydrophilic material.

16. A method according to claim 1, wherein the fluid pressure is selected from a range of fluid pressure values between approximately 50 millimeters of mercury and 100 millimeters of mercury.

17. A method according to claim 1, wherein the step of relieving the fluid pressure occurs after the expandable body member expands to the expanded state.

18. A method according to claim 1, further comprising the step of plugging the cervical opening before the step of providing the fluid to the uterine cavity.

19. An apparatus for delivering an expandable body member in a compressed state through a cervical opening and into a uterine cavity of a living body and deploying the expandable body member from the compressed state to an expanded state while the expandable body member is disposed in the uterine cavity, the apparatus comprising:

an elongated tubular member having a distal portion, a proximal portion and an intermediate portion disposed between the distal portion and the proximal portion, the distal portion and the expandable body member being connected together; and a fluid-providing device connected to the proximal portion of the elongated tubular member and operative to provide a fluid to the uterine cavity through the elongated tubular member at a sufficient pressure to inflate the uterine cavity to a volume larger than the expandable body member in the expanded state whereby the provided fluid causes the expandable body member to expand from the compressed state to the expanded state.

20. An apparatus according to claim 19, further comprising a plug element sized and adapted to plug the cervical opening in order to prevent the fluid from escaping the uterine cavity upon inflation, the plug element connected to the intermediate portion of the elongated tubular member.

21. An apparatus according to claim 20, further comprising a handle connected to the intermediate portion of the elongated tubular member.

22. An apparatus according to claim 21, wherein the handle is disposed between the plug element and the proximal portion of the elongated tubular member and includes an indicator for indicating to a user an approximate orientation of the expandable body member disposed within the uterine cavity.

23. An apparatus according to claim 22, wherein the elongated tubular member includes an articulating joint disposed between the handle and the plug element, the articulating joint operative to permit the elongated tubular member to bend.

24. An apparatus according to claim 19, wherein the fluid-providing device is a syringe assembly including a syringe.

25. An apparatus according to claim 24, wherein the syringe assembly includes a fitting operative to secure the syringe to the proximal portion of the elongated tubular member, the fitting connected to the proximal portion of the elongated tubular member.

26. An apparatus according to claim 19, wherein the fluid providing device is further operative to relieve the fluid pressure inside the uterine cavity after inflating the uterine cavity.

* * * * *